US00PP15592P3

(12) United States Plant Patent
Uchneat

(10) Patent No.: US PP15,592 P3
(45) Date of Patent: Feb. 22, 2005

(54) **DOUBLE *IMPATIENS* PLANT NAMED 'BALFIESINK'**

(50) Latin Name: *Impatiens walleriana*
Varietal Denomination: Balfiesink

(75) Inventor: Michael Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/737,402

(22) Filed: Dec. 16, 2003

(65) Prior Publication Data

US 2004/0226065 P1 Nov. 11, 2004

(51) Int. Cl.[7] ..... A01H 5/00

(52) U.S. Cl. ..... Plt./317

(58) Field of Search ..... Plt./317

*Primary Examiner*—Anne Marie Grunberg

(74) *Attorney, Agent, or Firm*—Wood, Phillips, Katz, Clark & Mortimer

(57) ABSTRACT

A new and distinct Double *Impatiens* plant named 'Balfiesink' characterized by its fully double dark pink/pale pink bicolor flowers, dark green-colored foliage, compact, upright and mounded growth habit and excellent basal branching.

1 Drawing Sheet

Latin name of genus and species of plant claimed: *Impatiens walleriana.*

Variety denomination: 'Balfiesink'.

BACKGROUND OF THE INVENTION

The present invention relates to a new and distinct cultivar of Double *Impatiens* plant botanically known as *Impatiens walleriana* and hereinafter referred to by the cultivar name 'Balfiesink'.

The new cultivar was developed by the inventor in a controlled breeding program during June 1999 at Elburn, Ill. The objective of the breeding program was to develop new *Impatiens* cultivars with numerous fully double flowers, excellent basal branching and upright compact growth habit.

The female (seed) parent of 'Balfiesink' was the proprietary *Impatiens walleriana* selection designated '3267c-3' (not patented) characterized by its vigorous growth habit, semi-double rose/white bicolor flowers and medium green foliage. The male (pollen) parent of 'Balfiesink' was the proprietary *Impatiens walleriana* selection designated '3309-1' (not patented) characterized by its vigorous upright habit, semi-double red/white bicolor flowers and dark green foliage. 'Balfiesink' was discovered and selected as one flowering plant within the progeny of the stated cross-pollination in February of 2000 and was initially designated '15799-2'.

Asexual reproduction of the new cultivar by terminal stem cuttings since February 2000 at West Chicago, Ill., has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any change in genotype.

It was repeatedly found that the cultivar of the present invention:

1. Exhibits fully double dark pink/pale pink bicolor flowers,
2. Forms dark green-colored foliage,
3. Exhibits a good basal branching character, and
4. Exhibits a compact, upright and mounded growth habit.

Plants of the new cultivar differ from plants of the parents primarily in flower form.

Of the many commercially available Double *Impatiens* cultivars known to the inventor, the most similar to 'Balfiesink' is 'Sparkler Rose' (U.S. Plant Pat. No. 9,630). However, in side-by-side comparisons, plants of the new cultivar differ from plants of 'Sparkler Rose' by the following characteristics:

1. Plants of the new cultivar have larger leaves of a lighter green color than plants of 'Sparkler Rose', and
2. The flowers of the plants of the new cultivar are redder in color than the flowers of the plants of 'Sparkler Rose'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs may differ slightly from the color values cited in the detailed description, which accurately describe the colors of 'Balfiesink'. The plants were grown for 8 weeks in a greenhouse at West Chicago, Ill.

DETAILED DESCRIPTION

Figure 1:
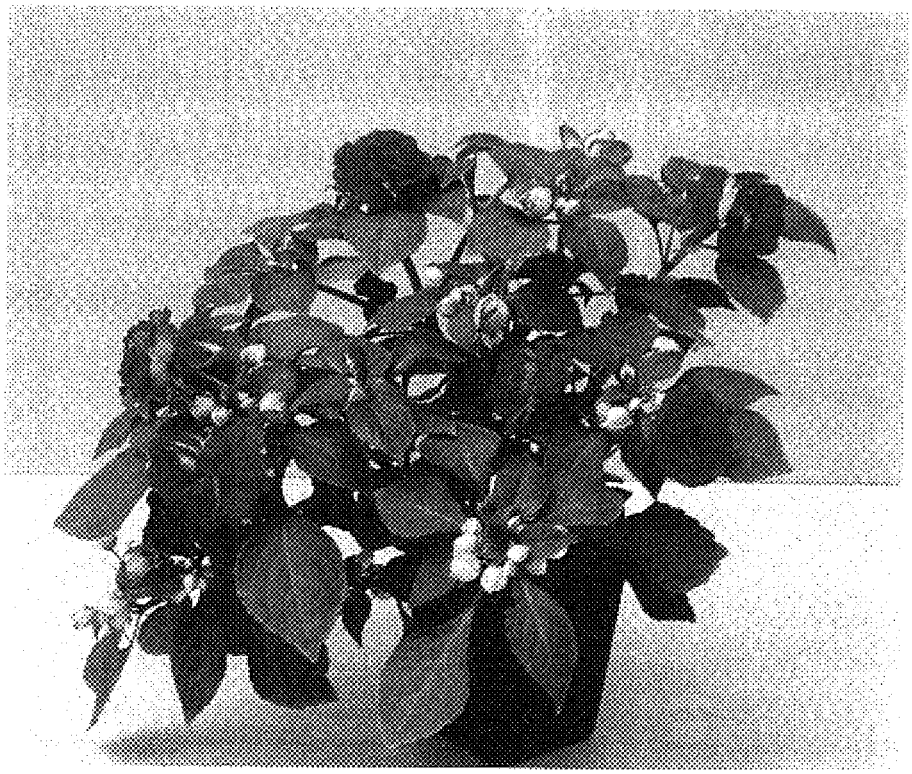
FIG. 1 illustrates a side view of the overall growth and flowering habit of 'Balfiesink'.
Figure 2:
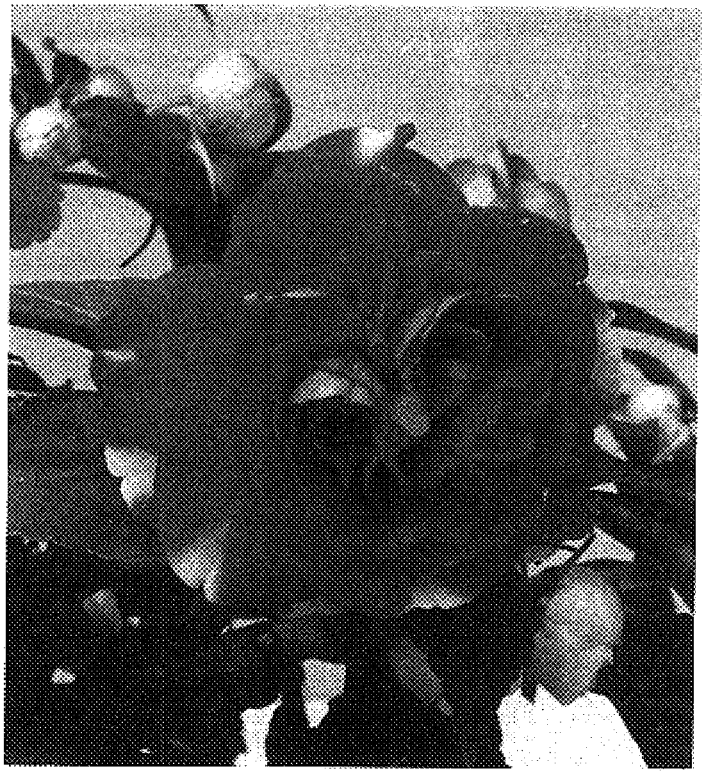
FIG. 2 illustrates a close-up view of an individual flower of 'Balfiesink'.

The chart used in the identification of colors described herein is the R.H.S. Colour Chart of The Royal Horticultural Society, London, England, 1995 edition, except where general color terms of ordinary significance are used. The color values were determined on Jul. 16, 2003 between 10:00 and 11:45 a.m. under natural light conditions.

The following measurements and comparisons describe plants produced from cuttings taken from stock plants and grown under greenhouse conditions comparable to those used in commercial practice. The plants were grown in 10 cm pots for 8 weeks while utilizing a soilless growth medium. Greenhouse temperatures were maintained at approximately 65°–75° F. during the day and approximately 55°–62° F. during the night. Greenhouse light levels were maintained at approximately 4,000–6,000 footcandles during the day.

Classification:

*Botanical.*—*Impatiens walleriana* cultivar 'Balfiesink'.

Parentage:

*Female* (*seed*) *parent.*—Proprietary *Impatiens walleriana* selection designated '3267c-3' (not patented).

*Male* (*pollen*) *parent.*—Proprietary *Impatiens walleriana* selection designated '3309-1' (not patented).

Propagation:

*Type cutting.*—Terminal stem.

*Time to initiate roots.*—Approximately 7–14 days with the shorter times generally being experienced in the summer and the longer times in the winter.

*Time to develop roots.*—Approximately 21 days.

*Root description.*—Fine, fibrous.

*Rooting habit.*—Freely branching.

Plant description:

*Habit of growth.*—Compact with good basal branching. A mature plant 8 weeks after the planting of a rooted cutting commonly measures approximately 26.2 cm in height and approximately 42.6 cm in width (plant spread).

*Plant form.*—Upright and mounded.

*Lateral branches.*—Quantity: Approximately 3 per plant. Length: Approximately 20.3 cm. Diameter: Approximately 1.3 cm. Texture: Glabrous. Color: 147C with splotches of 183B especially around nodes. Internode length: Approximately 3.2 cm.

*Foliage.*—Type: Simple. Arrangement: Alternate. Shape: Ovate. Apex: Acuminate. Base: Attenuate. Margin: Crenate/ciliate. Texture of both surfaces: Glabrous. Venation pattern: Pinnate, arcuate. Size of mature foliage: Length: Approximately 5.3 cm. Width: Approximately 3 cm. Color of mature foliage: Upper surface is slightly more yellow than 139A, with veins and mid-vein of 147C. Lower surface is 147B with blotches of 182B and veins and mid-vein of 147C. Petiole length: Approximately 1.8 cm. Petiole diameter: Approximately 2 mm. Petiole texture: Both surfaces are glabrous. Petiole color: 147C.

Flowering description:

*Flowering habit.*—Freely flowering.

*Natural flowering season.*—Year round in greenhouse environment. Flowering is continuous from spring until fall in the garden.

*Lastingness of individual bloom.*—Approximately 5–7 days.

*Quantity of flowers.*—Approximately 5 flowers and 8 buds per stem at any one time.

*Flower bud rate of opening.*—Generally it takes from 7 to 10 days for buds to progress from first color to fully open flowers.

*Mature flower buds* (*just before opening*).—Shape: Oval. Length: Approximately 1.6 cm. Diameter: Approximately 1.0 cm. Color of petals: 67A at margin and 69B at base.

*Flower description.*—Type: Fully double. Shape: Round. Diameter: Approximately 4.3 cm. Depth: Approximately 2.3 cm. Borne: Above foliage facing upward or outward. Flowers are not persistent or fragrant.

*Petals.*—Quantity per flower: Approximately 26. Shape: Obovate. Margin: Entire. Apex: Obtuse. Base: Attenuate. Texture: Smooth. Appearance: Iridescent. Size of outermost petals: Length: Approximately 2.5 cm. Width: 2.2 cm. Size of innermost petals: Length: 1.9 cm. Width: 1.6 cm.

*Flower color.*—Upper surface of petals when fully open: N66B with 71A at base. Lower surface of petals when fully open: N66D at margin gradually fading to N155B at base. Petal color fading with age to: Between 64A & N74A.

*Calyx.*—Quantity of sepals: Three, with the lower sepal modified into a spur. Sepal apex: Acuminate. Sepal texture: Both surfaces are glabrous. Lateral sepal shape: Lanceolate. Lateral sepal length: Approximately 4 mm. Lateral sepal width: Approximately 1 mm. Lateral sepal color: Both surfaces are 150A. Lower sepal shape: Ovate. Lower sepal length: Approximately 1 cm. Lower sepal width: Approximately 7 mm. Lower sepal color: Both surfaces are 150D with tip of 150B.

*Spur.*—Quantity: One per flower. Length: Approximately 2.7 cm. Diameter at base: Approximately 3 mm. Diameter at tip: Approximately 0.4 mm. Color: 150C with tip of 46A.

*Peduncles.*—Length: Approximately 1.6 cm. Diameter: Approximately 1 mm. Texture: Glabrous. Strength: Strong. Angle to stem: Acute. Color: Slightly lighter than 145B.

*Reproductive organs.*—None observed.

Seed and fruit development: Neither seed nor fruit production has been observed.

Disease and pest resistance: Resistance to pathogens and pests common to *Impatiens* has not been observed.

What is claimed is:

1. A new and distinct cultivar of Double *Impatiens* plant named 'Balfiesink' substantially, as herein shown and described, which:

1. Exhibits fully double dark pink/pale pink bicolor flowers,
2. Forms dark green-colored foliage,
3. Exhibits a good basal branching character, and
4. Exhibits a compact, upright and mounded growth habit.

* * * * *